United States Patent
Kirakossian et al.

(10) Patent No.: US 9,535,065 B2
(45) Date of Patent: Jan. 3, 2017

(54) METHODS AND COMPOSITIONS FOR CYTOMETRIC DETECTION OF RARE TARGET CELLS IN A SAMPLE

(75) Inventors: Hrair Kirakossian, San Jose, CA (US); Edward Goldberg, Los Gatos, CA (US); Diether Recktenwald, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 170 days.

(21) Appl. No.: 14/237,856

(22) PCT Filed: Sep. 6, 2012

(86) PCT No.: PCT/US2012/053933
§ 371 (c)(1),
(2), (4) Date: May 16, 2014

(87) PCT Pub. No.: WO2013/036620
PCT Pub. Date: Mar. 14, 2013

(65) Prior Publication Data
US 2014/0242610 A1 Aug. 28, 2014

Related U.S. Application Data

(60) Provisional application No. 61/531,575, filed on Sep. 6, 2011.

(51) Int. Cl.
*G01N 33/533* (2006.01)
*G01N 33/569* (2006.01)
(Continued)

(52) U.S. Cl.
CPC .... *G01N 33/56966* (2013.01); *G01N 15/1459* (2013.01); *G01N 33/533* (2013.01);
(Continued)

(58) Field of Classification Search
CPC .......... G01N 33/56966; G01N 33/57484; G01N 33/57496; G01N 15/1459; G01N 33/57492; G01N 33/533; G01N 33/56972; G01N 2015/1402; G01N 2015/1477
See application file for complete search history.

(56) References Cited

U.S. PATENT DOCUMENTS 7,332,288 B2 2/2008 Terstappen et al.
7,563,584 B2 * 7/2009 Perez .................. C12Q 1/485
422/73
(Continued)

FOREIGN PATENT DOCUMENTS

| CN | 101027557 A | 8/2007 |
| CN | 101583722 A | 11/2009 |
| WO | 2005078450 A2 | 8/2005 |

OTHER PUBLICATIONS

Amana et al. Quantitation of rare memory B cell populations by two independent and complementary approaches. Journal of Immunological Methods 317: 175-185 (2006).*
(Continued)

Primary Examiner — Gail R Gabel
(74) Attorney, Agent, or Firm — Bret E. Field; Bozicevic, Field & Francis LLP

(57) ABSTRACT

The present disclosure provides cytometric methods for the detection of rare target cells in a sample. In certain aspects, the methods and compositions may facilitate the detection of rare target cells, such as circulating tumor cells (CTCs), in a biological sample such as blood. Aspects of the methods include contacting the sample with first and second binding members that specifically bind to a marker of the rare target cell, and cytometrically assaying the sample for the presence of cells comprising bound first and second binding members to detect the rare target cell in the sample. Also provided are
(Continued)

systems, compositions, and kits for practicing the subject methods.

15 Claims, 11 Drawing Sheets

(51) Int. Cl.
*G01N 33/574* (2006.01)
*G01N 15/14* (2006.01)

(52) U.S. Cl.
CPC . *G01N 33/56972* (2013.01); *G01N 33/57484* (2013.01); *G01N 33/57492* (2013.01); *G01N 33/57496* (2013.01); G01N 2015/1402 (2013.01); G01N 2015/1477 (2013.01)

(56) References Cited

U.S. PATENT DOCUMENTS

| | | | |
|---|---|---|---|
| 7,785,810 B2 | 8/2010 | Chen | |
| 7,842,465 B2 | 11/2010 | Hsieh et al. | |
| 7,863,012 B2 | 1/2011 | Rao et al. | |
| 7,943,327 B2 * | 5/2011 | Purvis | G01N 33/5091 424/9.2 |
| 8,273,541 B2 * | 9/2012 | Chemin | C07K 16/2896 424/133.1 |
| 8,940,493 B2 * | 1/2015 | Gualberto | G01N 33/5023 435/7.23 |
| 2008/0057505 A1 | 3/2008 | Lin et al. | |
| 2009/0061456 A1 | 3/2009 | Allard et al. | |
| 2009/0098138 A1 | 4/2009 | Lorence | |
| 2010/0184083 A1 | 7/2010 | Panabieres et al. | |
| 2010/0323388 A1 | 12/2010 | Chiu et al. | |
| 2011/0110931 A1 | 5/2011 | Matsui | |
| 2011/0182881 A1 | 7/2011 | Chin et al. | |

OTHER PUBLICATIONS

Gullberg et al. Highly specific detection of phosphorylated proteins by Duolink, Nature Methods: vii-viii (Sep. 2009).*
Amanna et al. "Quantitation of rare memory B cell populations by two independent and complementary approaches", Journal of Immunological Methods, vol. 317, pp. 175-185 (2006).
Deng et al. "Enrichment with anti-cytokeratin alone or combined with anti-EpCAM antibodies significantly increases the sensitivity for circulating tumor cell detection in metastatic breast cancer patients", Breast Cancer Research, vol. 10, No. 4, p. R69 (2008).
Scibelli et al. "Fast track selection of immunogens for novel vaccines through visualisation of the early onset of the B-cell response", Vaccine, vol. 23, pp. 1900-1909 (2005).
Townsend et al. "Single epitope multiple staining to detect ultralow frequency B cells", Journal of Immunological Methods, vol. 249, pp. 137-146 (2001).
Masouleh et al. "Quantification of circulating endothelial progenitor cells in human peripheral blood: establishing a reliable flow cytometry protocol", J. Immunol. Methods. 2010, 357(1-2), 38-42.
Gerges; et al. "New technologies for the detection of circulating tumour cells", Br. Med. Bull. 2010, 94:49-64.
Brennan; et al. "Antibody-based proteomics: fast-tracking molecular diagnostics in oncology", Nat. Rev. Cancer 2010, 10(9):605-617.
Takao et al. "Enumeration, Characterization, and Collection of Intact Circulating Tumor Cells by Cross Contamination-Free Flow Cytometry", Cytometry, vol. 79A, No. 2, Feb. 1, 2011, pp. 107-117.
Chiorazzi et al. "Cellular origin(s) of chronic lymphocytic leukemia: cautionary notes and additional considerations and possibilities", Blood, vol. 117, No. 6, Feb. 10, 2011, pp. 1781-1791.

* cited by examiner

FIG. 4
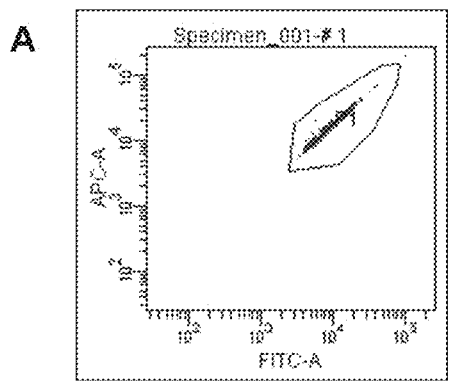
A
10,000 HT29 cells / mL
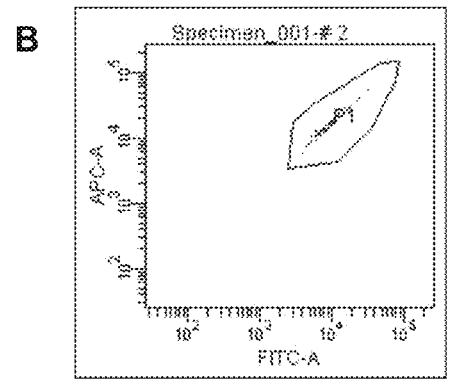
B
1,000 HT29 cells / mL
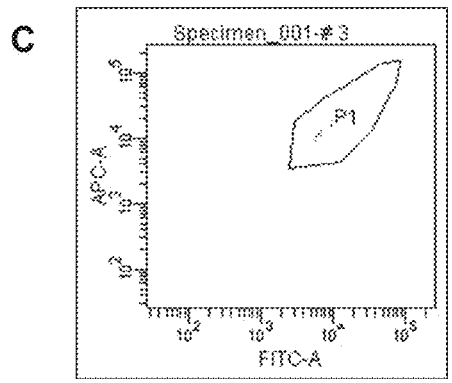
C
100 HT29 cells / mL
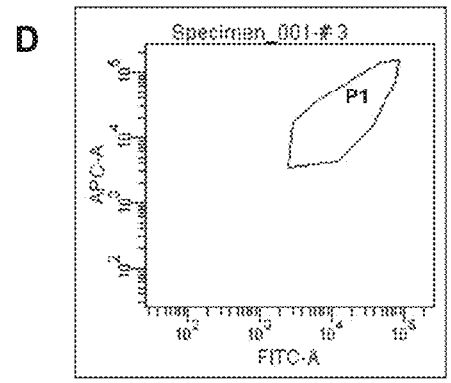
D
0.0 HT29 cells / mL

FIG. 5
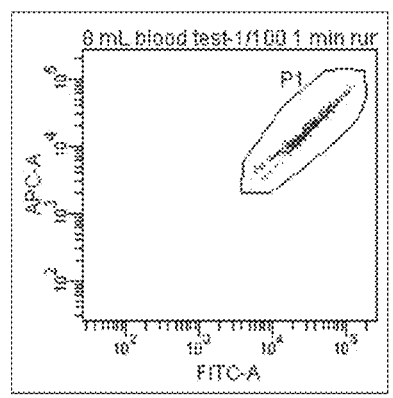
A
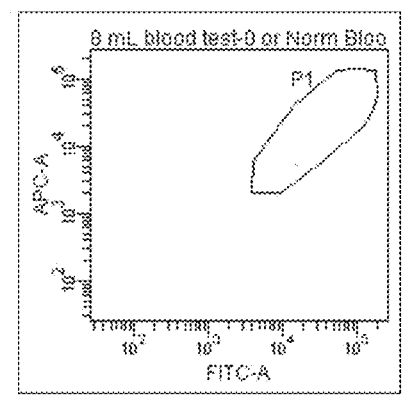
B
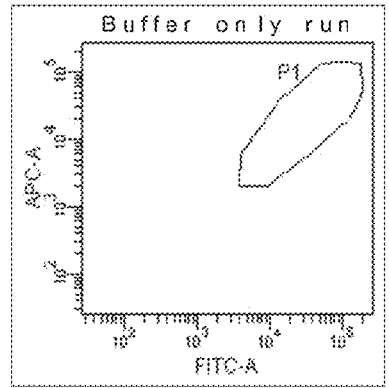
C

FIG. 9
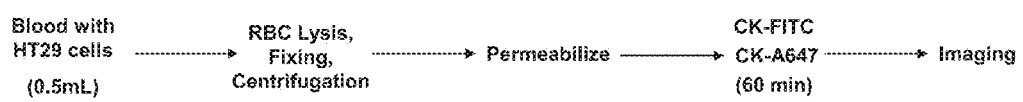
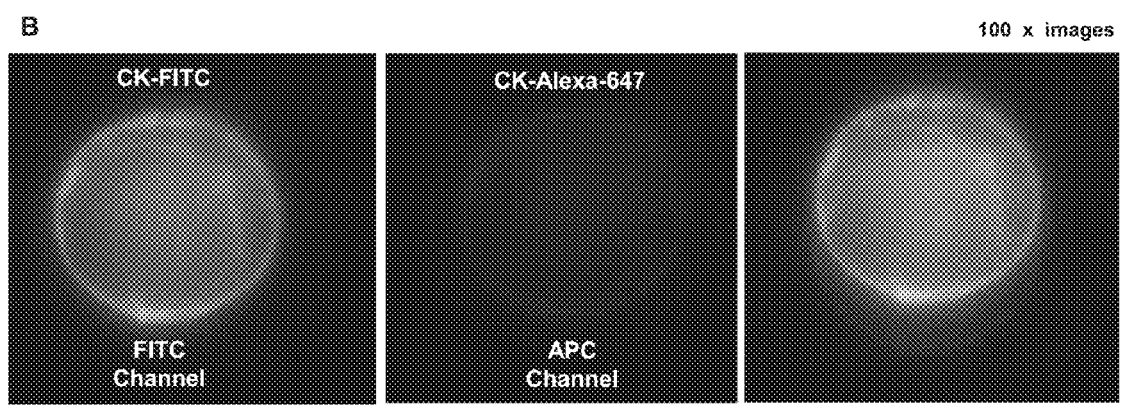

FIG. 10
Lysis – rep-1 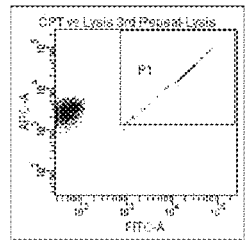
Lysis – rep-2 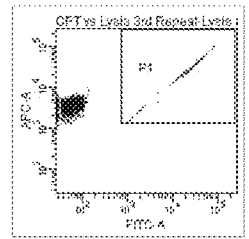

FIG. 10
(Continued)
CPT – rep-1 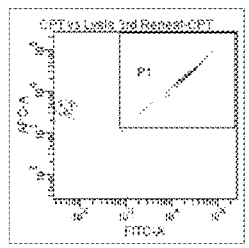
CPT – rep-2 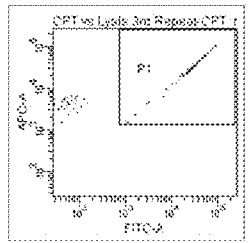

METHODS AND COMPOSITIONS FOR CYTOMETRIC DETECTION OF RARE TARGET CELLS IN A SAMPLE

CROSS-REFERENCE TO RELATED APPLICATIONS

Pursuant to 35 U.S.C. §119 (e), this application claims priority to the filing date of the U.S. Provisional Patent Application Ser. No. 61/531,575, filed Sep. 6, 2011, the disclosure of which is incorporated herein by reference.

INTRODUCTION

Flow cytometry is a well-accepted tool in research that allows a user to rapidly analyze and sort components in a sample fluid. Flow cytometers use a carrier fluid (e.g., a sheath fluid) to pass the sample components, substantially one at a time, through a zone of illumination. Each sample component is illuminated by a light source, such as a laser, and light scattered by each sample component is detected and analyzed. The sample components can be separated based on their optical and other characteristics as they exit the zone of illumination.

Circulating tumor cells (CTCs) are cells shed from tumors that enter into a subject's blood stream. Once in the blood, these cells can circulate through the subject's body, where they can invade other tissues and grow new tumors. CTCs are thus implicated in metastasis, which is the primary cause of death in subjects with cancer. Efforts to count CTCs have been hampered by the fact that CTCs are extremely difficult to detect: they are exceptionally rare, and may be difficult to distinguish from healthy cells. Existing approaches for detecting CTCs have limitations in sensitivity and/or specificity, leading to many healthy cells being mischaracterized as cancerous, and many cancer cells being missed in the analysis.

SUMMARY

The present disclosure provides cytometric methods for the detection of rare target cells in a sample. In certain aspects, the methods may facilitate the detection of rare target cells, such as circulating tumor cells (CTCs), in a biological sample such as blood. Aspects of the methods include contacting the sample with first and second binding members that specifically bind to a marker of the rare target cell, and cytometrically assaying the sample for the presence of cells comprising bound first and second binding members to detect the rare target cell in the sample. Also provided are systems, compositions, and kits for practicing the subject methods.

Rare target cells of interest include, but are not limited to, prokaryotic cells (e.g., bacterial cells or archaeal cells) and eukaryotic cells (e.g. mammalian cells, such as nerve cells, muscle cells, epithelial cells (e.g., circulating tumor cells), stem cells (e.g., hematopoietic stem cells), adipocyte cells and the like). Rare target cells may be detected from a range of samples, including samples obtained from an in vitro source (e.g., a suspension of cells from laboratory cells grown in culture) or from an in vivo source (e.g., a mammalian subject, a human subject, etc.).

A variety of binding members may be used in practicing the subject methods. A binding member may bind specifically to a marker of the rare target cell. Markers may of interest include, but are not limited to, CD1a, CD2, CD3, CD4, CD7, CD8, CD10, CD11b, CD13, CD14, CD15, CD16, CD19, CD20, CD22, CD23, CD25, CD30, CD33, CD34, CD38, CD41, CD45, CD56, CD57, CD59, CD61, CD64, CD71, CD74, CD79a, CD90, CD103, CD117, CD133, CD138, CD271, CD303, CD304, bcl-2, C-kit, TdT, FMC7, SCA-1, Glycophorin A, cytokeratins, EpCAM, EphB4, EGFR, CEA, HER2 and MUC-1. In certain aspects, a marker may be on the surface of the rare target cell, and/or inside the rare target cell. Nucleated cells may be permeablized to allow the first and second binding members to bind to an intracellular marker. In certain aspects of the subject methods, non-rare cells in the sample are not stained (e.g., are not stained for CD45).

In certain aspects, the binding members may be labeled. Labeling of a binding member may be direct, or indirect, as is described more fully herein. Labels of interest include, but are not limited to, indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, Alexa Fluor 700, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like.

Binding members of interest include antibodies, and antigen-binding fragments thereof. In some embodiments, where the first binding member and the second binding member are antibodies or antigen-binding fragments thereof, they bind to the same epitope of the marker.

Also provided by the present disclosure are kits. Kits may include first and second binding members that specifically bind to a marker of the rare target cell; instructions for using the first and second binding members to flow cytometrically assay the biological sample for the presence of cells comprising bound first and second binding members to detect the rare target cell in the sample. Compositions and systems are further provided, as described more fully herein.

BRIEF DESCRIPTION OF THE DRAWINGS

The invention may be best understood from the following detailed description when read in conjunction with the accompanying drawings. Included in the drawings are the following figures:

FIG. 4, Panels A-D are density plots showing enrichment and analysis of various concentrations of HT-29 tumor cells from blood in the presence of WBCs. Panel A: 0.5 mL blood samples containing 10,000 HT-29 cells/mL were subjected to red blood cell lysis, fixing and centrifugation. The WBC fraction was removed and permeabilized. CK-FITC and CK-Alexa647 were added for 60 m. The sample was analyzed using a BD Biosciences FACSCanto™ flow cytometer. Panel B: HT-29 cells were present at a starting concentration of 1,000 HT-29 cells/mL. Panel C: HT-29 cells were present at a starting concentration of 100 HT-29 cells/mL. Panel D: HT-29 cells were present at a starting concentration of 0 HT-29 cells/mL.

FIG. 5, Panels A-C are density plots showing enrichment and analysis of HT-29 tumor cells from blood in the presence of WBCs. Blood samples were lysed with 1×BD FACS Lysing solution to lyse red cells in the sample. The samples were permeabilized with 1×BD FACS Permeabilizing Solution 2, washed then stained intracellularly with CK Ab-FITC and CK Ab-A647 conjugates in 0.55 mL Rx volume and 0.36 mL of this mixture was counted without further washing, at medium (36 µL/min) flow rate on a BD Biosciences FACSCanto™ flow cytometer, according to the manufacturer's instructions. Panel A: Positive counts, using 7.5 mL blood and a concentration of 10,000 HT-29 cells/mL. Plot shows 1 minute counting. Panel B: Negative counts, using 7.5 mL blood and a concentration of 0 HT-29 cells/mL. Plot shows 10 minutes counting. Panel C: Buffer only, 15 minutes counting. Cumulatively, Panels A-C show one HT-29 tumor cell was observed on the background of 34,363,636 WBCs, and no false positive dot was registered for "Buffer only" during 15 minutes run.

FIG. 9, Panels A-B show the assay protocol and images of HT-29 tumor cells from blood in the presence of WBCs. Panel A: Assay procedure for imaging cells. Samples were prepared as described above in FIG. 5, and imaged using a ZEISS microscope using a mercury arc lamp. Panel B: From left to right: images of a CK-FITC containing cell (FITC Channel), a CK-Alexa647 containing cell (APC Channel), and an image overlay, respectively. All figures represent 100 images.

FIG. 10 shows plots comparing sample preparation techniques. Plots marked "Lysis" involve processing HT-29 tumor cells in blood using lysis and centrifugation. Plots marked "CPT" involve processing using BD Vacutainer CPT tubes.

DETAILED DESCRIPTION

Figure 1:
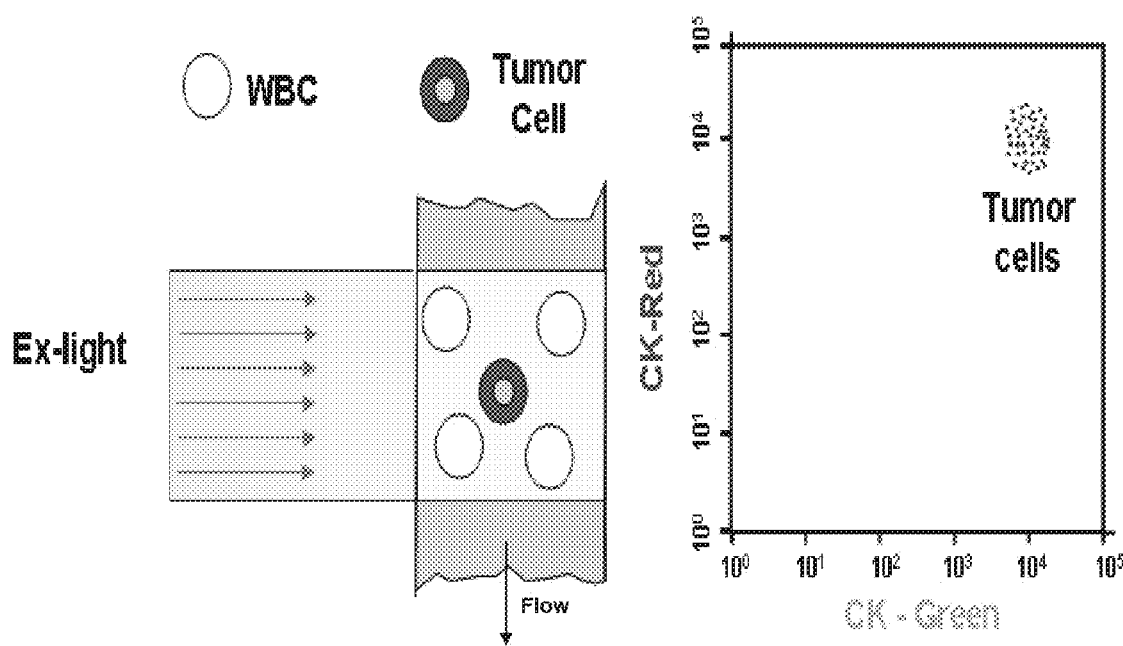
FIG. 1 is a graphical overview of a method according to the present disclosure. In this particular example, rare target cells (labeled as "Tumor Cells") are labeled with both cytokeratin (CK)-Red and CK-Green, while non-rare cells (here, white blood cells, or WBCs) are not labeled. The cells flow downward in a flow cytometer, as indicated by the arrows indicating flow. Excitation light ("Ex-light") is applied to cause fluorescence of CK-Red and/or CK-Green. The combination of two color fluorescence light, where each label is a fluorochrome, is used as the threshold in the flow cytometric assay. A resulting density plot of CK-Red fluorescence (y-axis) versus CK-Green fluorescence (x-axis) shows the number of tumor cells detected by the instrument.

The present disclosure provides cytometric methods for the detection of rare target cells in a sample. Aspects of the methods include contacting the sample with first and second binding members that specifically bind to a marker of the rare target cell, and cytometrically assaying the sample for the presence of cells comprising bound first and second binding members to detect the rare target cell in the sample. Also provided are systems, compositions, and kits for practicing the subject methods.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As described above, the present disclosure provides cytometric methods for the detection of rare target cells in a sample. The term "cytometric methods" is used herein to describe flow cytometric methods and/or imaging cytometric methods. Accordingly, "cytometric assay" may refer to a flow cytometric assay and/or imaging cytometric assay, and "cytometer" may refer to a flow cytometer and/or imaging cytometer.

Aspects of embodiments of the invention include contacting the sample with at least first and second binding members that specifically bind to a marker of the rare target cell. By interrogating the sample via cytometry to detect the presence of cells comprising bound first and second binding members, a rare target cell may be detected in the sample.

In some embodiments, methods of the invention of detecting a rare target cell in a sample are qualitative, where the detection of the rare target cell is qualitative, e.g., the determination is made that the target cell is or is not present in the sample. In some embodiments, methods of the invention of detecting a rare target cell in a sample are quantitative, where the detection of the rare target cell is quantitative. The methods can include determining a quantitative measure of the number of rare target cells in a sample. In some embodiments, quantifying the number of rare target cells in a sample includes determining whether the number of rare target cells present is above or below a predetermined threshold.

Various steps and aspects of the methods shall now be described in greater detail below.

Rare Target Cells

As described above, the present disclosure provides cytometric methods for the detection of rare target cells in a sample. As used herein, the term "rare target cells" is used to refer to any cell type present in a sample, where the number of cells of that type is less than 50.0% of the total number of cells of the sample, e.g., less than 40%, less than 30%, less than 20%, less than 10%, less than 1%, less than 0.1%, less than 0.01%, or less than 0.001%. In certain aspects, the rare target cells are outnumbered in the cellular sample by non-rare cells by a factor of $10^4$ or more, such as $10^5$ or more, including $10^6$ or more, $10^7$ or more, $10^8$ or more, or $10^9$ or more. Rare target cell types of interest include, but are not limited to, prokaryotic cells (e.g., bacterial cells or archaeal cells) and eukaryotic cells (e.g. mammalian cells, such as nerve cells, muscle cells, epithelial cells (e.g., circulating tumor cells), stem cells (e.g., hematopoietic stem cells), rare lymphocytes (e.g., regulatory T cells), adipocyte cells and the like).

The term "non-rare cells" may be used to refer to those cells of a sample that are not rare target cells. Non-rare cells may be of any type, including, but not limited to, prokaryotic cells (e.g., bacterial cells or archaeal cells) and eukaryotic cells (e.g. mammalian cells, such as nerve cells, white blood cells, muscle cells, epithelial cells, adipocyte cells and the like). In certain aspects of the subject methods, non-rare cells are not specifically labeled and/or stained prior to cytometric analysis. For example, in certain aspects non-rare cells are not CD45 stained. In certain aspects, non-rare cells may be substantially less labeled than are rare cells (e.g., due to nonspecific binding). In certain such aspects, rare cells may be distinguished from the substantially less labeled non-rare cells via cytometric analysis.

Samples

The terms "sample" and "cellular sample," as used herein means any sample containing one or more individual cells in suspension at any desired concentration. For example, the cellular sample can contain $10^{11}$ or less, $10^{10}$ or less, $10^9$ or less, $10^8$ or less, $10^7$ or less, $10^6$ or less, $10^5$ or less, $10^4$ or less, $10^3$ or less, 500 or less, 100 or less, 10 or less, or one cell per milliliter. The sample can contain a known number of cells or an unknown number of cells. Suitable cells include eukaryotic cells (e.g., mammalian cells) and/or prokaryotic cells (e.g., bacterial cells or archaeal cells).

In practicing the methods of the invention, the sample can be obtained from an in vitro source (e.g., a suspension of cells from laboratory cells grown in culture) or from and in vivo source (e.g., a mammalian subject, a human subject, etc.). In some embodiments, the cellular sample is obtained from an in vitro source. In vitro sources include, but are not limited to, prokaryotic (e.g., bacterial, archaeal) cell cultures, environmental samples that contain prokaryotic and/or eukaryotic (e.g., mammalian, protest, fungal, etc.) cells, eukaryotic cell cultures (e.g., cultures of established cell lines, cultures of known or purchased cell lines, cultures of immortalized cell lines, cultures of primary cells, cultures of laboratory yeast, etc.), tissue cultures, and the like.

In some embodiments, the sample is obtained from an in vivo source and can include samples obtained from tissues (e.g., cell suspension from a tissue biopsy, cell suspension from a tissue sample, etc.) and/or body fluids (e.g., whole blood, fractionated blood, plasma, serum, saliva, lymphatic fluid, interstitial fluid, etc.). In some cases, cells, fluids, or tissues derived from a subject are cultured, stored, or manipulated prior to evaluation. In vivo sources include living multi-cellular organisms and can yield non-diagnostic or diagnostic cellular samples.

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

Samples used in the instant methods may be obtained by any convenient method. In certain aspects, the sample is blood obtained via venipuncture. The blood may be obtained from a subject and be manipulated prior to cytometric analysis. Methods of obtaining and manipulating samples for cytometric analysis are well known in the art. For example, in certain aspects, samples may be manipulated using an assay as presented in FIG. 3. In this example, a blood sample is obtained by venipuncture from a subject following standard venipuncture protocols. The cellular sample is collected in a BD Vacutainer® CPT tube, and manipulated according to the manufacturer's instructions. The tube is centrifuged at about room temperature (about 18° C. to about 25° C.) for 20 minutes or more, at a Relative Centrifugal Force of about 1500 to about 1800. After centrifugation, the mononuclear cell layer and platelet layer are collected and resuspended. This fraction may be fixed and/or permeabilized using any convenient protocol, such as by using commercially available reagents such as BD FACS Permeabilizing Solution 2.

Binding Members

As described above, aspects of the invention may include contacting the sample with least first and second binding members that specifically bind to a marker of the rare target cell. The term "binding member" as used herein refers to any agent (e.g., a protein, small molecule, and the like) that specifically binds to a marker of the rare target cell. The terms "specific binding," "specifically binds," and the like, refer to the preferential binding to a molecule relative to other molecules or moieties in a solution or reaction mixture. In some embodiments, the affinity between binding member and the marker of the rare target cell to which it specifically binds when they are specifically bound to each other in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. "Affinity" refers to the strength of binding, increased binding affinity being correlated with a lower $K_d$.

In certain aspects of the invention, a sample may be contacted with more than two binding members that specifically bind to a marker of the rare target cell, e.g., 3 or more, 4 or more, 5 or more, 6 or more, 7 or more, 8 or more, 9 or more, including about 10 to 15, or about 15 or more.

Binding members may specifically bind to a marker of the rare target cell. As used herein, the term "marker" is used broadly and generically to refer to any molecule present on the surface of, or within, a rare target cell that is not normally present at the same concentration on healthy, non-rare cells as it is on rare target cells. In certain aspects, binding members may bind specifically to different markers of the rare target cell (e.g. different types of markers, such as EpCam and cytokeratin). In certain aspects, a marker may be present on the surface of a rare target cell. In other aspects, the marker is contained within the rare target cell. In such aspects, cells of the sample may need to be permeabilized so as to enable the first and second binding member to bind specifically to the intracellular marker. Methods of permeabilizing cells of a sample are well known in the art, and include, for example, commercial reagents and protocols, such as the use of BD FACS Permeabilizing Solution 2. Any convenient means of permeabilizing cells may be used in practicing the methods.

Markers of interest include, but are not limited to, CD1a, CD2, CD3, CD4, CD7, CD8, CD10, CD11b, CD13, CD14, CD15, CD16, CD19, CD20, CD22, CD23, CD25, CD30, CD33, CD34, CD38, CD41, CD45, CD56, CD57, CD59, CD61, CD64, CD71, CD74, CD79a, CD90, CD103, CD117, CD133, CD138, CD271, CD303, CD304, bcl-2, C-kit, TdT, FMC7, SCA-1, Glycophorin A, cytokeratins, EpCAM, EphB4, EGFR, CEA, HER2 and MUC-1.

In some embodiments, a binding member includes a label or a labeled binding member. As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, streptavidin or haptens), intercalating dyes and the like. The term "fluorescer" refers to a substance or a portion thereof which is capable of exhibiting fluorescence in the detectable range.

Labels of interest include both directly and indirectly detectable labels. Suitable labels for use in the methods described herein include any molecule that is indirectly or directly detectable by spectroscopic, photochemical, biochemical, immunochemical, electrical, optical, chemical, or other means. Labels of interest include, but are not limited to, fluorescein and its derivatives; rhodamine and its derivatives; cyanine and its derivatives; coumarin and its derivatives; Cascade Blue and its derivatives; Lucifer Yellow and its derivatives; BODIPY and its derivatives; and the like. Labels of interest also include fluorophores, such as indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, Alexa Fluor 700, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like.

Fluorescent labels can be detected using a photodetector (e.g., in a flow cytometer) to detect emitted light. Enzymatic labels are typically detected by providing the enzyme with a substrate and detecting the reaction product produced by the action of the enzyme on the substrate, colorimetric labels can be detected by simply visualizing the colored label, and antigenic labels can be detected by providing an antibody (or a binding fragment thereof) that specifically binds to the antigenic label. An antibody that specifically binds to an antigenic label can be directly or indirectly detectable. For example, the antibody can be conjugated to a label moiety (e.g., a fluorophore) that provides the signal (e.g., fluorescence); the antibody can be conjugated to an enzyme (e.g., peroxidase, alkaline phosphatase, etc.) that produces a detectable product (e.g., fluorescent product) when provided with an appropriate substrate (e.g., fluorescent-tyramide, FastRed, etc.); etc.

Figure 2:
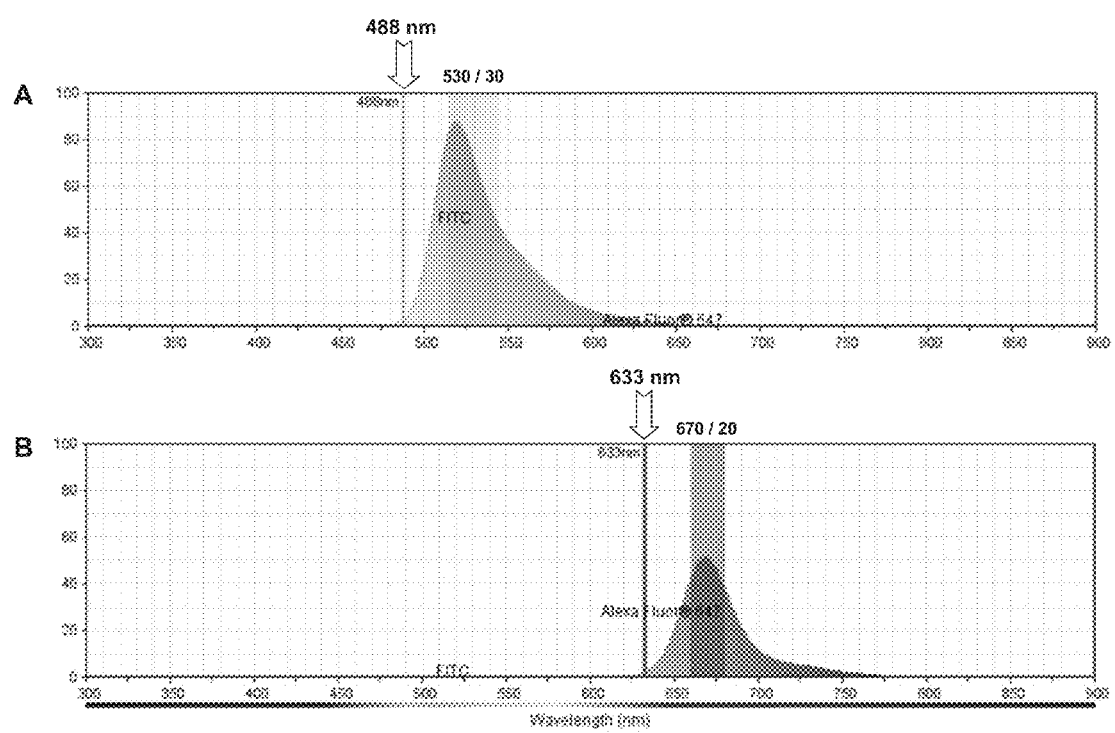
FIG. 2, Panels A-B depict the emission spectra for the labels fluorescein isothiocyanate (FITC; Panel A) and Alexa Fluor 647 (Panel B). The laser excitation line for each is indicated by an arrow.

The binding members of the methods may be labeled with different labels. In certain aspects, labels are selected so that the labels may be distinguished from one another, such as where the emission spectra of a first label and a second label do not substantially overlap. For instance, FIG. 2, Panels A-B depict the emission spectra for two labels that do not substantially overlap, fuorescein isothiocyanate (FITC; Panel A) and Alexa Fluor 647 (Panel B). FITC may be excited using light having a wavelength at about 488 nm, and its emission spectra may be detected using a filter (e.g., a 530/30 filter) that does not substantially overlap with the emission spectra of Alexa Fluor 647. Utilizing two different labels that have non-overlapping detectable emission spectra enables the resulting flow cytometric assay results to be plotted as a density plot of fluorescence of the first label on the y-axis versus fluorescence of the second label on the x-axis (See, e.g., FIG. 1).

In certain aspects, the binding members may be antibodies, or antigen-binding fragments thereof. As used herein, the term "antibodies" includes antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be further conjugated to other moieties, such as members of specific binding pairs, e.g., biotin (member of biotin-avidin specific binding pair), and the like. Also encompassed by the term are Fab', Fv, F(ab')$_2$, and or other antibody fragments that retain specific binding to antigen, and monoclonal antibodies.

Samples may be contacted with at least two binding members specific for the same marker of the rare target cell. Where the binding members are antibodies, the marker of the rare target cell may thus comprise one or more antigens that are bound by the antibodies. An "antigen" is a term that is well understood in the art, and includes any substance that may be specifically bound by an antigen-binding site of an antibody molecule or a T cell receptor. By "epitope" is meant a site on an antigen to which specific B cells and/or T cells respond. Antibodies that recognize the same epitope can be identified in a simple immunoassay showing the ability of one antibody to block the binding of another antibody to a target antigen. In certain aspects, the antibodies (e.g., the first binding member, second binding member, third binding member, etc.) bind the same epitope. In other aspects, the antibodies bind different epitopes.

A variety of binding members may be used for a given marker of interest. For example, where the marker of interest is CD45, binding members of interest include, but are not limited to, the commercially available antibodies produced by clone C0-F11, HI100, HI30, UCHL1, 30-F11, 2D1, L48, RA3-6B2 and D058-1283 (all BD Biosciences). However, in some instances the methods do not include staining for CD45.

Where the marker is a cytokeratin, binding members of interest include, but are not limited to, the commercially available antibodies produced by clone CAM5.2 that react primarily with human cytokeratin 7 and cytokeratin 8 (BD Biosciences); antibodies produced by clone KA4 that react primarily with human cytokeratins 14, 15, 16, and 19 (BD Biosciences); antibodies produced by clone RCK102 that react primarily with human, mouse, rat, hamster, pig, dog, and/or rabbit cytokeratins 5 and 8, as described in Lodish, et al. MCB, 2000, 795-847, the disclosure of which is incorporated herein by reference; antibodies produced by clone RCK105 that react primarily with human, mouse, rat, hamster, pig, and/or dog cytokeratin 7, as described in Lodish, et al (above); antibodies produced by clone AE1/AE3 (Millipore); antibodies produced by clone C-11, as described in Mikaelian, et al. (2004) Toxicol Pathol, 32: 181-191, the disclosure of which is incorporated herein by reference; antibodies produced by clone Lds103, as described in Southgate, et al. 1987 Lab. Invest., 56:211-223, the disclosure of which is incorporated herein by reference; and antibodies produced by clone CK2, as described in Wachter, et al. (1990) J. Hepatol., 11:232-239.

EpCAM binding members of interest include, but are not limited to, anti-EpCAM antibody BerEP4 as described in Sheibani, et al. *Am J Surg Pathol.* 1991 August; 15(8):779-784, the disclosure of which is incorporated herein by reference; KS1/4 as described in Antolovic, et al. (2010) *BMC Biotechnol* 10:35, the disclosure of which is incorporated herein by reference; antibodies produced by clone G8.8 that react primarily with mouse EpCAM (BD Biosciences); and antibodies produced by clone EBA-1 that react primarily with human EpCAM (BD Biosciences).

EGFR binding members of interest include, but are not limited to, antibodies produced by clone 13/EGFR; antibodies produced by clone 9H2; antibodies produced by clone EGFR.1; antibodies produced by clone 12A3; and antibodies produced by clone 17/eps15 (BD Biosciences).

CEA binding members of interest include, but are not limited to, antibodies produced by clone COL-1; antibodies produced by clone B1.1/CD66; and antibodies produced by clone B6.2/CD66 (BD Biosciences).

HER2 binding members of interest include, but are not limited to, antibodies produced by clone Neu24.7; antibodies produced by clone 42/c-erbB-2; antibodies produced by clone 3B5 (BD Biosciences); and antibodies produced by clone 9G6, as described in Hancock, et al. 1991 *Cancer Res.* 51:4575-4589, the disclosure of which is incorporated herein by reference.

MUC-1 binding members of interest include, but are not limited to, antibodies produced by clone HMPV (BD Biosciences).

Cytometric Analysis

Methods of the present disclosure may involve flow cytometrically assaying the sample. Flow cytometric assay procedures are well known in the art. See, e.g., Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem. January*; 49(pt 1):17-28; Linden, et. al., *Semin Throm Hemost.* 2004 October; 30(5):502-11; Alison, et al. *J Pathol,* 2010 December; 222(4):335-344; and Herbig, et al. (2007) *Crit Rev Ther Drug Carrier Syst.* 24(3):203-255; the disclosures of which are incorporated herein by reference. In certain aspects, flow cytometrically assaying the sample involves using a flow cytometer capable of simultaneous excitation and detection of multiple fluorophores, such as a BD Biosciences FACSCanto™ flow cytometer, used substantially according to the manufacturer's instructions. Methods of the present disclosure may involve image cytometry, such as is described in Holden et al. (2005) *Nature Methods* 2:773 and Valet, et al. 2004 *Cytometry* 59:167-171, the disclosures of which are incorporated herein by reference.

In certain aspects of the methods, the cytometric assay comprises forward light scattering (FSC) and/or side light scattering (SSC). In other aspects, the cytometric assay comprises detecting both the label of the first binding member and the label of the second binding (FIG. 4, Panels A-D and FIG. 5, Panels A-C), where instead of scattered light the combination of the labels (e.g., the combination of two color fluorescence light, where each label is a fluorochrome) is used as the threshold in the assay. In such aspects, identification of a rare target cell in the sample may require detection of both the first label and the second label. In certain aspects, identification of a rare target cell in the sample may require detection of more than two labels (e.g., a third binding member, a fourth binding member, etc.).

In certain aspects, non-rare cells may be separated from a sample prior to cytometric analysis. Any convenient means of removing non-rare cells from a sample may be employed. Separation methods of interest include, but are not limited to, magnetic separation techniques, such as those described in U.S. Pat. Nos. 5,945,281, 6,858,440; 6,645,777; 6,630,355; and 6,254,830; US Patent Application No. PCT/US2012/032423; and Hoeppener, et al. (2012) Recent Results Cancer Res. 195:43-58; the disclosures of which are incorporated herein by reference. Separation methods of interest further include those comprising acoustic concentrators or separators, such as those described in U.S. Pat. No. 6,929,750, the disclosure of which is hereby incorporated by reference.

Cytometric analysis may comprise sorting. Cells identified in the sample as rare target cells may be sorted and subsequently analyzed by any convenient analysis technique. Subsequent analysis techniques of interest include, but are not limited to, sequencing; assaying by CellSearch, as described in Food and Drug Administration (2004) Final rule. Fed Regist 69: 26036-26038; assaying by CTC Chip, as described in Nagrath, et al. (2007) *Nature* 450: 1235-1239; assaying by MagSweeper, as described in Talasaz, et al. (2009). *Proc Natl Acad Sci USA* 106: 3970-3975; and assaying by nanostructured substrates, as described in Wang S, et al. (2011) *Angew Chem Int Ed Eng/*50: 3084-3088; the disclosures of which are incorporated herein by reference. Where desired, the sorting protocol may include distinguishing viable and dead rare cells, where any convenient staining protocol for identifying such cells may be incorporated in to the methods.

Systems

Also provided are cytometric systems for practicing the subject methods. The cytometric systems may include a cytometric sample fluidic subsystem, as described below. In addition, the cytometric systems include a cytometer fluidically coupled to the cytometric sample fluidic subsystem. Systems of the present disclosure may include a number of additional components, such as data output devices, e.g., monitors, printers, and/or speakers, data input devices, e.g., interface ports, a mouse, a keyboard, etc., fluid handling components, power sources, etc.

In certain aspects, a cytometric system includes a cytometric sample fluidic subsystem configured to contact a sample comprising a rare target cell with first and second binding members that specifically bind to a marker of the rare target cell. The subsystem may be further configured such that non-rare cells of the sample are not specifically labeled and/or stained (e.g., are not stained for CD45). Systems may include a cytometer fluidically coupled to the cytometric sample fluidic subsystem.

In other aspects, systems may include a cytometric sample fluidic subsystem configured to contact a sample comprising a rare target cell with first and second binding members that specifically bind to a marker of the rare target cell; and a cytometer fluidically coupled to the flow cytometric sample fluidic subsystem, the cytometer configured to assay the sample for the presence of cells comprising bound first and second binding members to detect the rare target cell in the sample. In certain aspects, the cytometer is configured to use the combination of fluorescence of a first label attached to the first binding member and a second label attached to the second binding member as a detection threshold.

Kits

Also provided are kits for practicing one or more embodiments of the above-described methods. The subject kits may include various components and reagents. In some instances, the kits include at least reagents finding use in the methods (e.g., as described above); and a computer readable medium having a computer program stored thereon, wherein the computer program, when loaded into a computer, operates the computer to perform a cytometric assay as described herein; and a physical substrate having an address from which to obtain the computer program.

In addition to the above components, the subject kits may further include instructions for practicing the methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., CD, DVD, Blu-Ray, flash memory, etc., on which the information has been recorded. Yet another means that may be present is a website address which may be used via the Internet to access the information at a removed site. Any convenient means may be present in the kits.

Utility

The subject methods, compositions, systems and kits find use in a variety of different applications where it is desirable to detect rare target cells in a sample.

Non-limiting exemplary embodiments of the present disclosure are provided as follows:

1. A method of detecting a rare target cell in a sample, the method comprising:
   contacting the sample with first and second binding members that specifically bind to a marker of the rare target cell, and
   cytometrically assaying the sample for the presence of cells comprising bound first and second binding members to detect the rare target cell in the sample.
2. The method according to 1, wherein cytometrically assaying the sample comprises flow cytometrically assaying the sample.
3. The method according to 1 or 2, wherein cytometrically assaying the sample comprises image cytometrically assaying the sample.
4. The method according to any of 1-3, further comprising contacting the sample with a third binding member that specifically bind to a marker of the rare target cell, and cytometrically assaying the sample for the presence of cells comprising bound first, second, and third binding members to detect the rare target cell in the sample.
5. The method according to any of 1-4, wherein at least the first and second binding members are antibodies, or antigen-binding fragments thereof.
6. The method according to 5, wherein the antibodies or antigen-biding fragments thereof bind to overlapping epitopes on the marker
7. The method according to 6, wherein the antibodies or antigen-biding fragments thereof bind to the same epitope of the marker.
8. The method according to any of 1-7, wherein the binding members are labeled.
9. The method according to 8, wherein the binding members are directly labeled.
10. The method according to any of 8-9, wherein the first or second binding member is labeled with a label selected from indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, Alexa Fluor 700, JOE, Lissamine, Rhodamine Green, BODIPY, fluorescein isothiocyanate (FITC), carboxyfluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, and RiboGreen.
11. The method of any of any of 8-10, wherein the label of the first binding member and the label of the second binding member are different labels.

12. The method according to any of 1-11, wherein non-rare cells in the sample are not specifically stained.
13. The method according to any of 1-12, wherein non-rare cells in the sample are not stained for CD45.
14. The method according to any of 1-13, wherein the marker is an intracellular marker.
15. The method according to 14, comprising permeabilizing nucleated cells in the sample with a permeabilizing agent.
16. The method according to any of 1-15, wherein the marker is selected from CD1a, CD2, CD3, CD4, CD7, CD8, CD10, CD11b, CD13, CD14, CD15, CD16, CD19, CD20, CD22, CD23, CD25, CD30, CD33, CD34, CD38, CD41, CD45, CD56, CD57, CD59, CD61, CD64, CD71, CD74, CD79a, CD90, CD103, CD117, CD133, CD138, CD271, CD303, CD304, bcl-2, C-kit, TdT, FMC7, SCA-1, Glycophorin A, cytokeratins, EpCAM, EphB4, EGFR, CEA, HER2 and MUC-1.
17. The method according to any of 1-16, wherein the sample is blood.
18. The method according to any of 1-17, wherein the sample is whole blood.
19. The method according to any of 1-18, wherein the sample is obtained from a mammalian subject.
20. The method according to any of 1-19, wherein the sample is obtained from a human subject.
21. The method according to any of 1-20, wherein the rare target cell is an epithelial cell.
22. The method according to 21, wherein the epithelial cell is a circulating tumor cell.
23. The method according to 22, wherein the marker is a cytokeratin selected from CK4, CK7, CK8, CK10, CK13, CK14, CK18, CK19, and CK20.
24. The method according to 22, wherein the first and second binding members are antibodies, and bind substantially the same epitope as an antibody produced by clone CAM5.2, KA4, RCK102, RCK105, C-11, Lds103, or CK2.
25. The method according to any of 1-24, wherein cytometrically assaying the sample comprises sorting.
26. The method according to 25, wherein the rare target cell is collected.
27. The method according to 26, wherein the rare target cell is subsequently assayed.
28. A cellular sample comprising:
   a rare target cell comprising a marker; and
   first and second binding members that specifically bind to the marker of the rare target cell.
29. The cellular sample according to 28, further comprising a third binding member that specifically binds to the marker of the rare target cell.
30. The cellular sample according to 28 or 29, wherein the binding members are antibodies, or antigen-binding fragments thereof.
31. The cellular sample according to 30, wherein the antibodies or antigen-biding fragments thereof bind to overlapping epitopes on the marker
32. The cellular sample according to 31, wherein the antibodies or antigen-biding fragments thereof bind to the same epitope of the marker.
33. The cellular sample according to any of 28-32, wherein the binding members are labeled.
34. The cellular sample according to 33, wherein the binding members are directly labeled.
35. The cellular sample according to any of 33-34, wherein the first or second binding member is labeled with a label selected from indocarbocyanine (C3), indodicarbocyanine (C5), Cy3, Cy3.5, CyS, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, Alexa Fluor 700, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, and RiboGreen.
36. The cellular sample of any of any of 33-35, wherein the label of the first binding member and the label of the second binding member are different labels.
37. The cellular sample according to any of 28-35, wherein non-rare cells in the sample are not specifically stained.
38. The cellular sample according to any of 28-37, wherein non-rare cells in the sample are not stained for CD45.
39. The cellular sample according to any of 28-38, wherein the marker is an intracellular marker.
40. The cellular sample according to any of 28-39, wherein the marker is selected from CD1a, CD2, CD3, CD4, CD7, CD8, CD10, CD11b, CD13, CD14, CD15, CD16, CD19, CD20, CD22, CD23, CD25, CD30, CD33, CD34, CD38, CD41, CD45, CD56, CD57, CD59, CD61, CD64, CD71, CD74, CD79a, CD90, CD103, CD117, CD133, CD138, CD271, CD303, CD304, bcl-2, C-kit, TdT, FMC7, SCA-1, Glycophorin A, cytokeratins, EpCAM, EphB4, EGFR, CEA, HER2 and MUC-1.
41. The cellular sample according to any of 28-40, wherein the sample is blood.
42. The cellular sample according to any of 28-41, wherein the sample is whole blood.
43. The cellular sample according to any of 28-42, wherein the sample is obtained from a mammalian subject.
44. The cellular sample according to any of 28-43, wherein the sample is obtained from a human.
45. The cellular sample according to any of 28-44, wherein the rare target cell is an epithelial cell.
46. The cellular sample according to 45, wherein the epithelial cell is a circulating tumor cell.
47. A cytometric system comprising:
   a cytometric sample fluidic subsystem configured to contact a sample comprising a rare target cell with first and second binding members that specifically bind to a marker of the rare target cell, wherein non-rare cells of the sample are not labeled; and
   a cytometer fluidically coupled to the cytometric sample fluidic subsystem.
48. The cytometric system of 47, wherein the cytometric sample fluid subsystem is a flow cytometric sample fluid subsystem, and the cytometer is a flow cytometer.
49. A cytometric system comprising:
   a cytometric sample fluidic subsystem configured to contact a sample comprising a rare target cell with first and second binding members that specifically bind to a marker of the rare target cell; and
   a cytometer fluidically coupled to the cytometric sample fluidic subsystem, the cytometer configured to assay the sample for the presence of cells comprising bound first and second binding members to detect the rare target cell in the sample.
50. The cytometric system of 49, wherein the cytometric sample fluid subsystem is a flow cytometric sample fluid subsystem, and the cytometer is a flow cytometer.
51. A kit for identifying a rare target cell in a sample, the kit comprising:
first and second binding members that specifically bind to a marker of the rare target cell;
instructions for using the first and second binding members to flow cytometrically assay the biological sample for the presence of cells comprising bound first and second binding members to detect the rare target cell in the sample.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Materials and Methods

The following are general materials and protocols used in Examples below.

Purified anti-cytokeratin antibodies were obtained from BD (Franklin Lakes, N.J.). Antibodies were separated into two populations, and two populations of fluorochrome-conjugated anti-cytokeratin antibodies were produced by conjugating FITC or Alexa Fluor 647 fluorochromes to the antibodies of a population, respectively. HT-29 colon adenocarcinoma cells were obtained from ATCC (ATCC HTB 38).

Blood samples were lysed using 1×BD FACS Lysis solution. Samples were permeabilized using 1×BD FACS Permeabilizing Solution 2. All flow cytometric assays were performed using a BD Biosciences FACSCanto™ flow cytometer. All reagents and materials were used following manufacturer's protocols.

Example 1

Detection of Tumor Cells in Blood Samples

Figure 3:
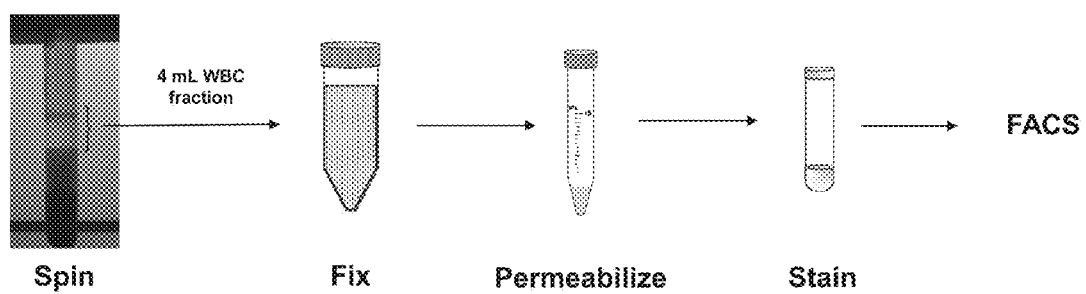
FIG. 3 is a flowchart of an assay procedure of the present disclosure. A 7.5 mL sample is spun in a BD Vacutainer CPT tube according to the manufacturer's instructions to separate the WBC portion. The WBC fraction is subsequently fixed, permeabilized, stained, and analyzed via FACS, such as by a BD Biosciences FACSCanto™ flow cytometer.

Venous blood of normal donors was collected in sodium heparin BD Vacutainer tubes. HT-29 tumor cells were added to blood samples at concentrations of (i) 10,000 HT-29 cells/mL; (ii) 1,000 HT-29 cells/mL; (iii) 100 HT-29 cells/mL; or (iv) 0 HT-29 cells/mL. For each of the four samples, a 7.5 mL draw was taken and spun in a BD Vacutainer CPT tube to separate the WBC portion. The CPT sample preparation technique was comparable to a protocol involving lysis and centrifugation (FIG. 10). The WBC fraction was subsequently fixed, permeabilized, stained with CK-FITC and CK-Alexa647 for 60 m, and analyzed via FACS (FIG. 3).

The resulting density plots (FIG. 4, Panels A-D) of APC channel (y-axis) versus FITC channel (x-axis) showed a population of cells in the samples where HT-29 tumor cells had starting concentrations of (i) 10,000 HT-29 cells/mL (Panel A); (ii) 1,000 HT-29 cells/mL (Panel B); and (iii) 100 HT-29 cells/mL (Panel C). The number of cells observed in each plot decreased in proportion to the starting concentration of the HT-29 tumor cells. No cells were observed in where the starting HT-29 tumor cell concentration was 0 cells/mL (Panel D).

HT-29 tumor cells could be detected even when the background of WBCs was high (FIG. 5, Panels A-C). Blood samples (7.5 mL) containing HT-29 cells at a concentration of 10,000 cells/mL were lysed with 1×FACS Lysis solution, permeabilized with 1×BD FACS Permeabilizing Solution 2, washed then stained with CK Ab-FITC and CK Ab-A647 conjugates in 0.55 mL Rx volume and 0.36 mL of this mixture was counted without further washing, at medium (36 µL/min) flow rate on a BD Biosciences FACSCanto™ flow cytometer. One HT-29 tumor cell was observed on the background of 34,363,636 WBCs (Panels A-B), and no false positive dot was registered for "Buffer only" during 15 minutes run (Panel C).

Figure 6:
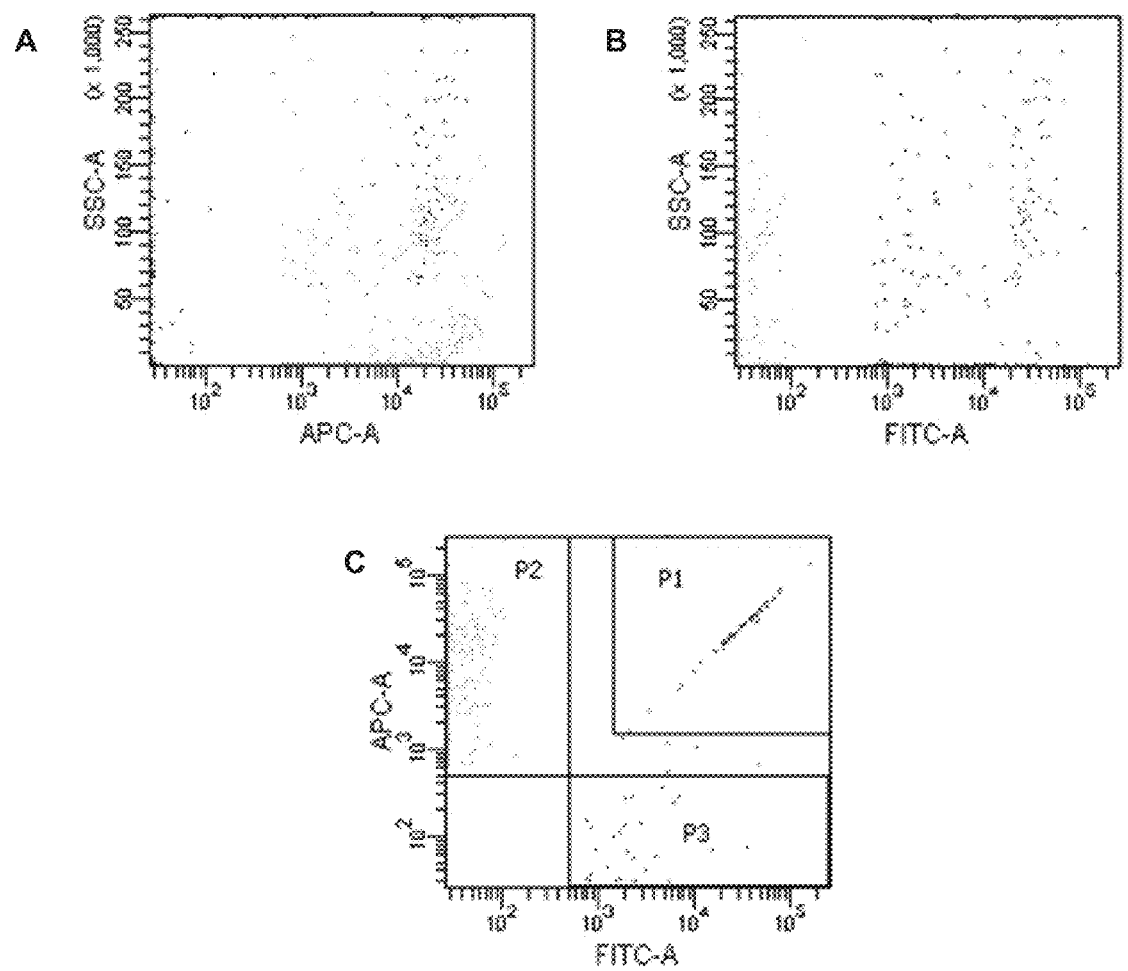
FIG. 6, Panels A-C show the discrimination efficiency of methods of the present disclosure. Samples containing WBC and HT-29 tumor cells were prepared as describe herein, and labeled with CK-APC and CK-FITC. Panels A and B: typical one-color density plots showing SSC versus APC (Panel A) and FITC (Panel B). HT-29 tumor cells are represented by darker dots in the plots, and could not be easily detected from nonspecific events. Panel C: measuring both APC and FITC in the samples leads to a narrow-diagonally descending dot-plot, and the tumor cells are easily identified.
Figure 7:
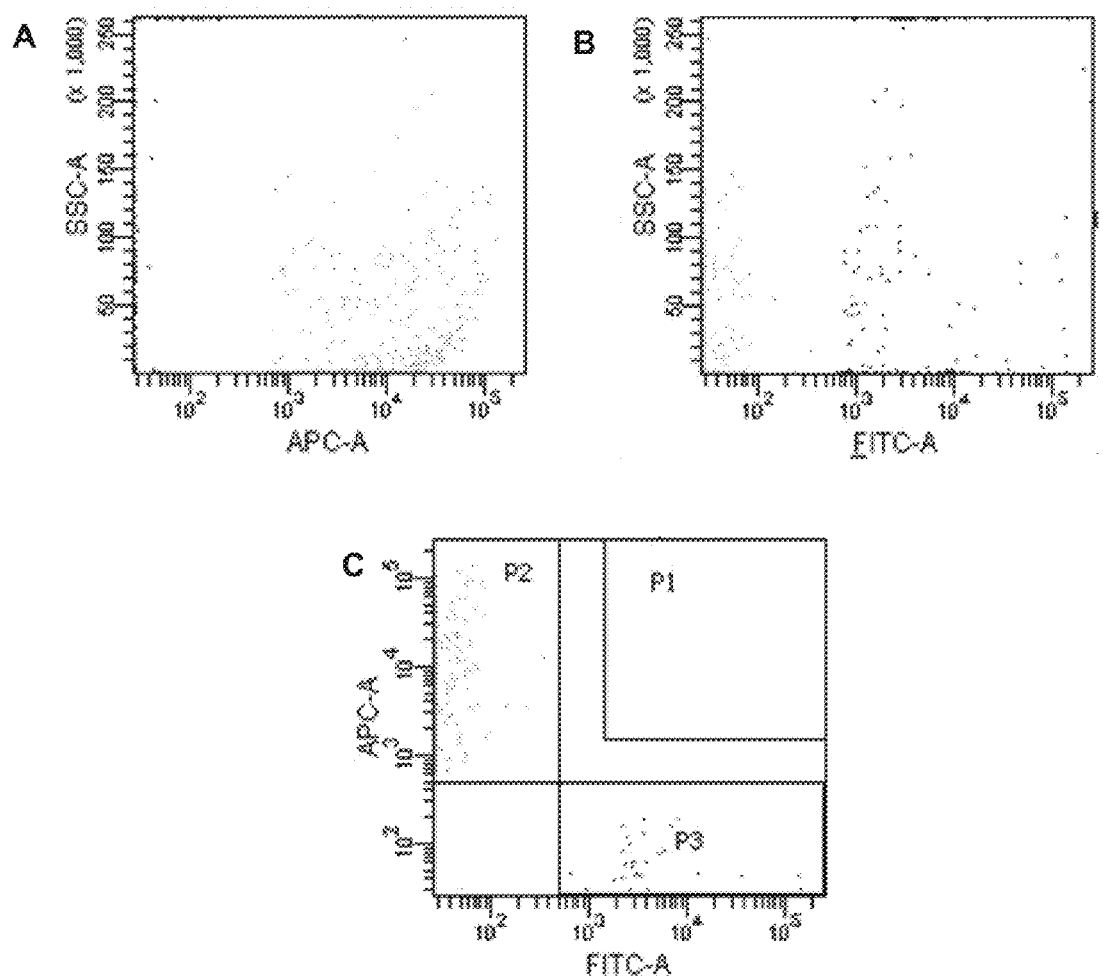
FIG. 7, Panels A-C show negative samples of the samples of FIG. 6. No HT-29 tumor cells were present in these samples. Panels A and B: one-color density plots showing SSC versus APC (Panel A) and FITC (Panel B) revealed many false positives. Panel C: no false positive events were observed.

Discrimination of HT-29 cells from false positive events was improved by requiring the detection at least a first and second binding member. For example, HT-29 tumor cells could not be easily detected from nonspecific events when the binding of only one binding member was observed (FIG. 6, Panels A-B; FIG. 7, Panels A-B). Requiring detection of at a first and second binding member led to a narrow-diagonally descending dot plot and easy identification of HT-29 cells (FIG. 6, Panel C), while also eliminating false positive events (FIG. 7, Panel C).

Figure 8:
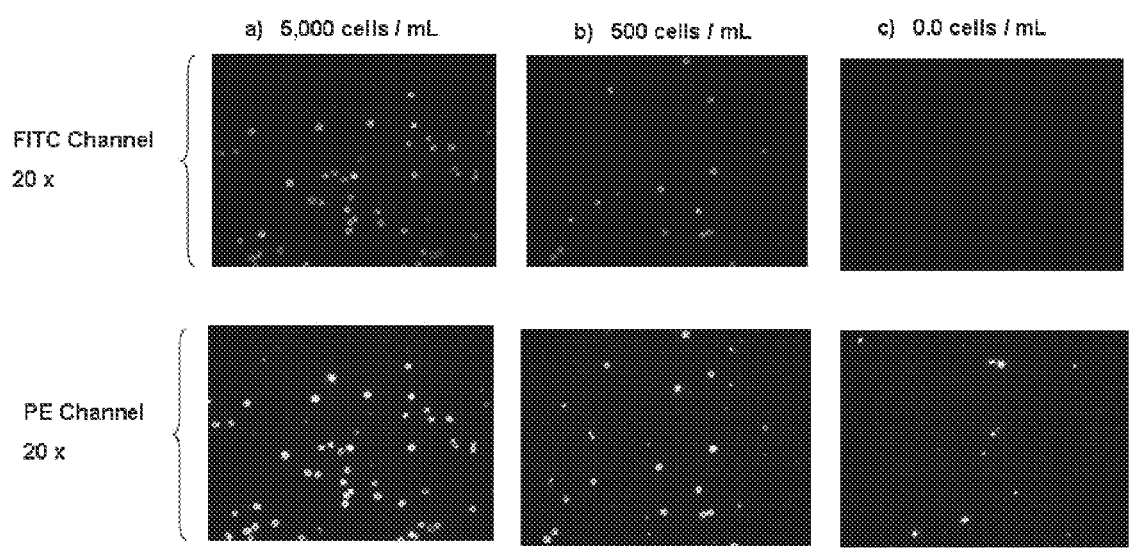
FIG. 8, Panels A-C show images of HT-29 tumor cells in samples, using various starting concentrations. Samples containing WBC and HT-29 cells were stained with CK-FITC and CK-PE. HT-29 cells were present at concentrations of 5,000 cells/mL (Panel A), 500 cells/mL (Panel B), or 0.0 cells/mL (Panel C). Events were observed in the PE channel even at HT-29 cell concentrations of 0.0 cells/mL (Panel C).

Imaging further revealed that many false positive events may be observed by measuring only one binding member. For instance, FIG. 8, Panels A-C show images of HT-29 tumor cells at various starting concentrations. Samples containing WBC and HT-29 tumor cells were stained with CK-FITC and CK-PE. HT-29 cells were present at concentrations of 5,000 cells/mL (Panel A), 500 cells/mL (Panel B), or 0.0 cells/mL (Panel C). Events were observed in the PE channel even at HT-29 cell concentrations of 0.0 cells/mL (Panel C).

Individual cells were also imaged, using a ZEISS microscope and a mercury arc lamp (FIG. 9, Panels A-B). Samples were prepared as described above, and individual cells were imaged using a ZEISS microscope using a mercury arc lamp. Images taken from the FITC channel revealed the presence of CK-FITC in individual cells, the APC channel revealed the presence of CK-Alexa647 in the individual cells, and the overlay showed both CK-FITC and CK-Alexa647 present in the cell (right image, Panel B). 100 images were taken of each sample.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of detecting a rare tumor cell in a sample, the method comprising:
    contacting the sample with distinguishably fluorescently labeled first and second binding members that specifically bind to the same target epitope of a marker in or on the rare tumor cell to produce a labeled sample comprising both of the fluorescently labeled first and second binding members, and
    cytometrically assaying the labeled sample for the presence of cells comprising epitope bound first and second binding members to detect the rare tumor cell in the sample.

2. The method according to claim 1, wherein the first and second binding members are antibodies, or antigen-binding fragments thereof.

3. The method according to claim 1, wherein non-rare cells in the sample are not labeled.

4. The method according to claim 1, comprising permeabilizing nucleated cells in the sample with a permeabilizing agent.

5. The method according to claim 4, wherein the target epitope is an intracellular epitope.

6. The method according to claim 1, wherein the target epitope is an epitope of cytokeratin.

7. The method according to claim 1, wherein the marker having the same target epitope is selected from the group consisting of CD1a, CD2, CD3, CD4, CD7, CD8, CD10, CD11b, CD13, CD14, CD15, CD16, CD19, CD20, CD22, CD23, CD25, CD30, CD33, CD34, CD38, CD41, CD45, CD56, CD57, CD61, CD64, CD71, CD74, CD79a, CD103, CD117, CD133, CD138, CD271, CD303, CD304, bcl-2 (B-cell lymphoma 2), TdT (terminal deoxynucleotidyl transferase), FMC7, Glycophorin A, cytokeratins, EpCAM (epithelial cell adhesion molecule), (carcinoembryonic antigen), HER2 (human epidermal growth factor receptor 2) and MUC-1 (mucin 1).

8. The method according to claim 1, wherein the sample is whole blood.

9. The method according to claim 1, wherein the sample is obtained from a human.

10. The method according to claim 1, wherein the target epitope is a cell-surface epitope.

11. The method according to claim 1, wherein the distinguishably labeled first and second binding members have non-overlapping detectable emission spectra.

12. The method according to claim 1, wherein the rare tumor cell is a circulating tumor cell.

13. The method according to claim 1, wherein non-rare cells in the sample are separated from the sample prior to cytometric analysis.

14. A composition comprising a cellular sample comprising:
    a rare tumor cell comprising a marker having a target epitope; and
    distinguishably fluorescently labeled first and second binding members that specifically bind to the target epitope of the marker in or on the rare tumor cell, wherein the cellular sample is a human whole blood sample.

15. A kit for cytometrically identifying a rare tumor cell in a sample, the kit comprising:
    distinguishably fluorescently labeled first and second binding members that specifically bind to the same target epitope of a marker in or on the rare tumor cell, wherein the marker is selected from the group consisting of CD1a, CD2, CD3, CD4, CD7, CD8, CD10, CD11 b, CD13, CD14, CD15, CD16, CD19, CD20, CD22, CD23, CD25, CD30, CD33, CD34, CD38, CD41, CD45, CD56, CD57, CD61, CD64, CD71, CD74, CD79a, CD103, CD117, CD133, CD138, CD271, CD303, CD304, bcl-2 (B-cell lymphoma 2), TdT (terminal deoxynucleotidyl transferase), FMC7, Glycophorin A, a cytokeratin, EpCAM (epithelial cell adhesion molecule), (carcinoembryonic antigen), HER2 (human epidermal growth factor receptor 2) and MUC-1 (mucin 1);
    instructions for using the first and second binding members to cytometrically assay a labeled sample for the presence of cells comprising epitope bound first and second binding members to detect the rare tumor cell in the sample.

* * * * *